(12) United States Patent  
Durm et al.

(10) Patent No.: US 10,775,343 B2
(45) Date of Patent: Sep. 15, 2020

(54) METHOD FOR OPERATING A MEASUREMENT SITE, AND MEASUREMENT SITE

(71) Applicant: Endress+Hauser Conducta GmbH+Co. KG, Gerlingen (DE)

(72) Inventors: Oliver Durm, Benningen am Neckar (DE); Martin Lohmann, Gerlingen (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 134 days.

(21) Appl. No.: 16/032,297

(22) Filed: Jul. 11, 2018

(65) Prior Publication Data

US 2019/0017960 A1 Jan. 17, 2019

(30) Foreign Application Priority Data

Jul. 12, 2017 (DE) .................. 10 2017 115 663

(51) Int. Cl.
*G05B 23/00* (2006.01)
*G01N 27/416* (2006.01)
(Continued)

(52) U.S. Cl.
CPC ..... *G01N 27/4165* (2013.01); *G01N 27/4167* (2013.01); *G05B 19/0423* (2013.01);
(Continued)

(58) Field of Classification Search
CPC .. G01N 21/274; G01N 21/93; G01N 27/3274; G01N 33/0006; G01N 27/4175
See application file for complete search history.

(56) References Cited

U.S. PATENT DOCUMENTS 8,744,547 B2* 6/2014 Budiman ........... A61B 5/14532
600/347

FOREIGN PATENT DOCUMENTS

DE         69925069 T2    3/2006
DE      202006010007 U1   8/2006
(Continued)

OTHER PUBLICATIONS

Search Report for German Patent Application No. 10 2017 115 663.1, German Patent Office, dated Mar. 23, 2018, 6 pp.

*Primary Examiner* — Alexander S Noguerola
(74) *Attorney, Agent, or Firm* — Kelly J. Smith; Endress+Hauser (USA) Holding Inc.

(57) ABSTRACT

The present disclosure relates to a method for operating a measurement site for determining at least one measurand of a medium, wherein the measurement site has at least one sensor unit, in contact with the medium, for detecting measured values, and an operating unit with a display element, wherein the sensor unit is connected wirelessly or by wire to the operating unit for communication, wherein the method includes the steps of determining a first value that represents a remaining time span up to a specified time point for a maintenance measure to be performed on the sensor unit; determining a second value that represents a current state of the sensor unit; determining a third value, based at least upon the first and second values, that represents a recommended action with regard to the sensor unit; and displaying the third value or a symbol derived therefrom, or a signal derived from the third value, by means of the display element.

14 Claims, 2 Drawing Sheets

(51) Int. Cl.
*G05B 19/042* (2006.01)
*G05B 23/02* (2006.01)
*G01N 27/327* (2006.01)
*G01N 21/27* (2006.01)
*G01N 33/00* (2006.01)

(52) U.S. Cl.
CPC ....... *G01N 21/274* (2013.01); *G01N 27/3274* (2013.01); *G01N 33/0006* (2013.01); *G05B 23/0283* (2013.01); *G05B 2219/25428* (2013.01)

(56) References Cited

FOREIGN PATENT DOCUMENTS

| | | |
|---|---|---|
| DE | 102009055093 A1 | 6/2011 |
| DE | 102013114393 A1 | 6/2015 |

* cited by examiner

METHOD FOR OPERATING A MEASUREMENT SITE, AND MEASUREMENT SITE

CROSS-REFERENCE TO RELATED APPLICATION

The present application is related to and claims the priority benefit of German Patent Application No. 10 2017 115 663.1, filed on Jul. 12, 2017, the entire contents of which are incorporated herein by reference.

TECHNICAL FIELD

The present disclosure relates to a method for operating a measurement site, and a measurement site for determining at least one measurand of a medium, wherein the measurement site has at least one sensor unit, in contact with the medium, for detecting measured values, and an operating unit with a display element, and wherein the sensor unit is connected wirelessly or by wire to the operating unit for communication.

BACKGROUND

Such measurement sites are, for example, pH measurement sites, or other measurement sites for analytical measurement. This can include, in particular, other potentiometric, amperometric, coulometric, colorimetric, photometric, turbidimetric, and spectrometric sensor units.

A sensor unit comprises at least one transducer that emits an electrical signal dependent upon the value of the measurand. Frequently, the transmission function of the transducer is variable. This holds true, especially, for pH sensors. Consequently, pH sensors must be serviced at appropriate time points—especially, recalibrated. The length of the time intervals between the maintenance measures or the calibration intervals strongly depends upon environmental influences to which the sensor is exposed over its lifespan. The overall life expectancy is also strongly influenced by these environmental conditions (hereinafter also termed the load or sensor load).

In pH measurement and also in analytical measurement, the term, "calibration," is frequently used differently than is customary. Generally, a calibration is understood to be the check of the display of a measuring device against a standard, and the deviation between the true value and displayed value is identified. Matching the displayed value with the true value is termed adjustment. The measure that is normally termed calibration in pH measurement and analytical measurement is, strictly speaking, an adjustment. Since this language is, however, routine in these fields, it will also be used here and in the following.

In the prior art, a plurality of measures is known for equipping sensors with intelligent self-diagnosis. There is a series of approaches for predicting a time point at which a maintenance measure of a sensor unit should be performed. For example, an adaptive calibration timer is known from DE 101 41 408 A1 that iteratively adapts a specified basic calibration interval for a pH sensor as a function of the temperature and pH load to which the sensor unit is exposed. A method is known from WO 2004/025223 A2 by means of which a residual life of the sensor unit is forecast from an extrapolation of the calibration parameters of the pH sensor unit determined repeatedly in the past, i.e., the zero point and slope of the sensor characteristic. A method is known from DE 10 2004 012420 A1 in which a history of the pH and temperature load that a sensor unit experiences over its operating life is saved in the form of a load matrix, and displayed. Operating hours meters are also known that record and add up the operating hours during which a sensor unit has been exposed to a temperature above a specific threshold, or to a pH below or above a specific threshold.

Today, operating units such as measuring transducers or portable operating devices that can be connected by wire or wirelessly to a sensor unit for communication and can be used at measurement sites in analytical engineering—especially in the processing industry—generally offer several such diagnostic functions. They are to help a user schedule the maintenance of the individual sensor units, so that maintenance measures can be performed in a timely manner, before the respective sensor units no longer provide reliable measured values, and so that set maintenance intervals are not exceeded. However, a user requires a lot of experience to interpret the various diagnostic results, which are generally presented on several displays which are separate from each other, such as in the form of several bar charts and possibly additional displayed numeric values, and to relate them to each other to achieve this goal.

SUMMARY

It is therefore the aim of the present disclosure to present a method for operating a measurement site, and a measurement site that facilitates the maintenance of the sensor unit, or several sensor units, of the measurement site—especially, the timely scheduling of maintenance measures—to ensure the reliability of the measured values provided by the measurement site, and to maintain set maintenance intervals.

This aim is achieved according to the present disclosure by the method according to claim 1, and the measurement site according to claim 13. Possible embodiments are indicated in the dependent claims.

The method according to the present disclosure is a method for operating a measurement site for determining at least one measurand of a medium, wherein the measurement site has at least one sensor unit, in contact with the medium, for detecting measured values, and an operating unit with a display element, and wherein the sensor unit is connected wirelessly or by wire to the operating unit for communication. It comprises the steps of:

determining a first value that represents a remaining time span up to a specified time point for a maintenance measure to be performed on the sensor unit—especially, a calibration;
  determining a second value that represents a current state of the sensor unit;
  determining a third value, based at least upon the first and second values, that represents a recommended action with regard to the sensor unit; and
  displaying the third value or a symbol derived therefrom, or a signal derived from the third value, by means of the display element.

Both the first and second values provide a user with information as to whether prompt maintenance of the sensor unit is needed, or whether the sensor unit can still operate over a longer time period without a maintenance measure. Because a third value that represents a recommended action with regard to the sensor unit is determined and displayed, a user now has the option of drawing upon the third value to schedule measures—especially, maintenance measures—for the sensor unit. He no longer has to derive necessary measures from the first and second values solely on the basis of his experience. Moreover, determining and displaying the third value enables a clearer representation of a recommended action, since the first and second values can be omitted on the display.

In determining the third value, other values can also be included which can be determined from the various self-diagnosis functions of the sensor unit.

Any operating or control device for communication that can be connected to the sensor unit directly, or via one or more intermediate devices or electronics for communication, can serve as the operating unit. For example, the operating unit can be a measuring transducer connected to the sensor electronics of the sensor unit. In another example, the sensor unit can be releasably or permanently connected to a control device that need not necessarily have its own display and that is connected for communication directly or indirectly to a higher-level unit such as a process control. In addition, an—in particular—portable control device such as, for example, a tablet computer, smart phone, smart watch, or data glasses that is connected to the control device for communication—especially, wirelessly—can be the operating unit in this case.

The steps of determining the first value, and/or the second value, and/or the third value can be performed by the operating unit. Alternatively, it is also possible for electronics of the sensor unit that are connected to the operating unit for communication to participate in calculating the first, second, or third value. Values that are included in the calculation of the first or second value can also be saved in the sensor unit. It is also possible for the steps of determining the first value, and/or the second value, and/or the third value to be performed in a higher-level unit connected to the operating unit for communication—for example, in a process control center or a cloud.

The first value can be determined by a comparison of a time span that has passed since a last-performed maintenance, such as a calibration, of the sensor unit with a specified value of a service interval especially specified for the sensor unit, such as a calibration interval. The service interval is preferably specified such that it corresponds to a time span in which the measuring error of the sensor unit from an age-related change in the transmission function still remains within a tolerance interval. The service interval is, accordingly, preferably specified, depending upon the environmental conditions predominating at the measurement site (such as temperature fluctuations, chemical composition of the medium, contaminant load in the medium), and depending upon the type of sensor unit. This specification can, for example, be done by a user, or be established by regulatory specifications. The service interval can also be adaptively customizable, as described in DE 101 41 408 A1. The type of sensor unit is determined by the measurand that is detected by the sensor unit, such as the pH, ion concentration, concentration of a dissolved gas such as oxygen, or conductivity. Moreover, if the type of sensor unit is determined by the sensor unit design and the associated specification, there are, for example, certain types of pH sensor units that can better resist temperature loads than other types of pH sensor units. In an advantageous embodiment of the method, the operating unit can read out an identifier of the sensor unit from a memory—which, for example, can be a component of the sensor unit electronics—securely connected to the sensor unit, which identifier comprises information on the type of the sensor unit, and a calibration interval can be automatically specified by using the read out identifier. For this, the operating unit can, for example, access a database that contains an assignment of a suitable service interval to the sensor type.

The second value can be determined from current values of parameters correlated with the state of the sensor unit, and/or from values, repeatedly detected in the past, of parameters that represent a development of the state of the sensor unit, and/or an—in particular, thermal and/or chemical—load on the sensor unit occurring during a service life of the sensor unit. Parameters correlated to the sensor unit state can, for example, be current technical parameters such as a membrane impedance of a sensor unit comprising a sensor membrane, or a zero point and/or slope of a sensor characteristic, or a sensor unit response time. Values of these parameters can be repeatedly detected during the sensor service life, such as in each calibration, and saved as a history. The values saved in the history can be included in the second value as a development of the values representing the state. Parameters that represent a load on the sensor unit occurring during a service life of the sensor unit can, for example, be a temperature curve, a pH value curve, a number of hours during which the temperature of the sensor unit lay above a threshold value, and a number of hours during which the sensor unit was exposed to a pH above a first threshold value and/or below a second threshold value.

To determine the third value, the first and the second values can each be compared with one or more threshold values that are specified or can be specified by the user, wherein, based upon the result of the comparisons with the threshold values, a value is selected as a third value from several different specified values that represent different recommended actions. Three values, for example, can be specified, i.e., "no action necessary," "action soon necessary," and "action presently recommended." Based upon the comparison of the first and second values to one or more threshold values, the operating unit can determine whether and with what urgency a maintenance measure is needed, and can select the corresponding one of the three values.

The third value can be output by means of the display element as a signal that is visually detectable by a user. The display element can, for example, have a display, and the third value can be presented on the display as a symbol that is visually detectable by a user. Of course, the third value can also be depicted on the display as alphanumeric text. It is also possible for the display element to have a light source such as a lamp or one or more LED's that can display several different visual signals, which each stand for one of the specified values. The operating element can, for this purpose, control the light source. The optical signals can, for example, be colored light signals, or a flashing frequency.

In the event that the third value represents a recommended action that includes the performance of a service measure on the sensor unit, additionally, a time point that lies in the future can be determined for performing the service measure.

The display element can display the time point lying in the future, or the remaining time span up to the time point lying in the future, and/or can output a signal representing the time span. If the determined third value is, for example, the recommended action, "maintenance soon necessary," a time span, e.g., as an alphanumeric text, can also be displayed within which maintenance is recommended. A signal representing the time span can, for example, be a frequency with which a symbol displayed on the display that represents a recommended action appears and disappears.

In one embodiment, the measurement site can comprise several sensor units connected to the operating unit for communication, wherein, for each of the several sensor units, the following are determined:

A first value representing a remaining time span up to a specified time for a service measure to be performed on the sensor unit—especially, calibration—a second value representing a current state of the sensor unit, and, based at least upon the first and second values, a third value that represents a recommended action with regard to the sensor unit, wherein the third value is output by means of the display element. If the several sensor units belong to different sensor types, the employed first and second values can be determined according to calculation rules correspondingly tailored to the respective sensor type, and the recommended actions can also be tailored to the existing sensor type so that correspondingly different recommended actions are output for sensory units of the different type. It is, however, also possible to standardize the values representing the recommended actions, in order to improve the clarity of the display.

In one possible embodiment of the measurement site, a first sensor unit of the several sensor units can belong to a first sensor type, and a second sensor unit of the several sensor units can belong to a second sensor type different from the first sensor type. In this case, for the first sensor unit:
  the first value can be determined by a comparison of a time span that has passed since a last-performed maintenance—especially, calibration—of the first sensor unit with a specified value of a first service interval—especially, a first calibration interval; and
  by means of a first calculating rule, the second value can be determined from current values of first parameters correlated with the state of the first sensor unit, and/or from values, repeatedly detected in the past, of first parameters that represent a development of the state of the first sensor unit, or a load on the first sensor unit occurring during a service life of the first sensor unit.

Correspondingly, for the second sensor unit:
  the first value can be determined by a comparison of a time span that has passed since a last-performed maintenance—especially, calibration—of the second sensor unit with a specified value of a second service interval—especially, a calibration interval—that differs from the first service interval—especially, a calibration interval; and
  by means of a second calculation rule that differs from the first calculation rule, the second value can be determined from current values of second parameters correlated with the state of the second sensor unit, and/or from values, repeatedly detected in the past, of second parameters that represent a development of the state of the second sensor unit, or a load on the second sensor unit occurring during a service life of the second sensor unit.

By way of illustration, if the first sensor unit is a pH glass electrode and the second sensor unit is an inductive conductivity sensor, service intervals that differ in length for the pH glass electrode and inductive conductivity sensor can be provided, given the environmental conditions predominating at the measurement site, because, for example, the environmental conditions predominating at the measurement site more strongly affect the measuring accuracy of the pH class electrode than that of the conductivity sensor. Accordingly, in this case, the specified service interval for the pH glass electrode is shorter than that for the conductivity sensor. The second values of the pH glass electrode and the inductive conductivity sensor representing the sensor state are also calculated differently, both with regard to the parameters included in the second value and in terms of the calculation rules for determining the second value from the values of the included parameters.

The display element can comprise a display, as mentioned. In this case, when several sensor units are present for outputting the third values determined for each of the several sensor units, an identifier of each of the sensor units, together with the associated determined third value, can be presented on the display combined in a list. Accordingly, a user can see all of the determined actions at a glance and schedule service measures without having to know or take into account the different calculation rules or different service intervals.

The present disclosure also relates to a measurement site for determining at least one measurand of the medium, comprising:
  at least one sensor unit in contact with a medium for detecting measured values;
  wherein the sensor unit comprises at least one transducer that is configured to output an electrical signal dependent upon the value of the measurand, and a sensor circuit that is configured to output the electrical signal of the transducer or a signal derived from the electrical signal of the transducer as a measurement signal to the operating unit; and
  an operating unit that comprises electronics, and a display element that can be controlled by the electronics,
  wherein the electronics are configured to receive and process the measurement signal, and comprise at least one processor and one memory in which is saved software that can be run by the electronics and that is configured to implement the method according to one of claims 1 through 12.

The operating unit can be connected directly or indirectly by wire or wirelessly—especially, by radio—to the sensor unit or to a control device that, for its part, is connected to the sensor unit.

In an advantageous embodiment, the measurement site comprises at least two sensor units connected to the operating device, as already mentioned beforehand in conjunction with the method according to the present disclosure. A first of the sensor units can belong to a first sensor type, whereas the second of the sensor units belongs to a second sensor type different from the first sensor type. For the first sensor unit, the software can be configured:
  to determine the first value by a comparison of a time span that has passed since a last-performed maintenance of the first sensor unit with a specified value of a first service interval; and
  to determine by means of a first calculation rule the second value from current values of first parameters correlated with the state of the first sensor unit, and/or from values, repeatedly detected in the past, of first parameters that represent a development of the state of the first sensor unit, or a load on the first sensor unit occurring during a service life of the first sensor unit, and, for the second software unit:
  to determine the first value by a comparison of a time span that has passed since a last-performed calibration of the second sensor unit with a specified value of a second calibration interval that differs from the first calibration interval; and
  by means of a second calculation rule that differs from the first calculation rule, to determine the second value from current values of second parameters correlated with the state of the second sensor unit, and/or from values, repeatedly detected in the past, of second parameters that represent a development of the state of the second sensor unit, or a load on the second sensor unit occurring during a service life of the second sensor unit.

BRIEF DESCRIPTION OF THE DRAWINGS

The present disclosure is explained in further detail below on the basis of the embodiment shown in the figures. Shown are.

DETAILED DESCRIPTION

Figure 1:
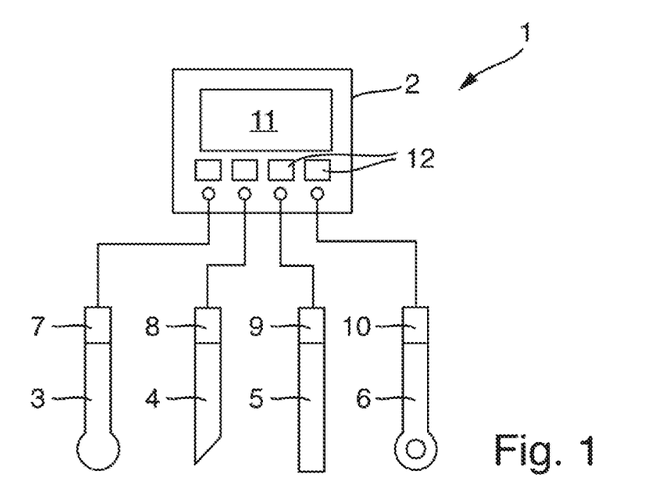
FIG. 1 shows a schematic representation of a measurement site with two pH sensor units of different types, and two conductivity sensor units of different types.

FIG. 1 schematically represents a measurement site 1 with four sensor units 3, 4, 5, 6 of different sensor types, and an operating unit 2 connected to the sensor units for communication. A first sensor unit 3 comprises a pH glass electrode with a transducer for generating an electrical signal that depends upon the pH of a medium in contact with the transducer. A second sensor unit 4 is also designed to measure pH, wherein the transducer of the second sensor unit has a pH-sensitive ISFET. A third sensor unit 9 serves to measure the conductivity of a medium that is in contact with it and comprises a transducer based upon a conductive measuring principle. A fourth sensor unit 6 is also configured to measure conductivity and has a transducer that functions according to an inductive measuring principle, to generate electrical measurement signals. When the measurement site 1 is in measuring mode, all four sensor units are in contact with the medium in order to measure and monitor its pH or conductivity. The medium can, for example, be held in a process vessel such as a conduit or fermenter. To contact the medium, the sensor units can be integrated in a wall of the container, e.g., with the assistance of fittings.

The sensor units 3, 4, 5, 6 each comprise sensor electronics 7, 8, 9, 10 that are each accommodated in an electronics housing. The sensor electronics in the present example are connected via cables to the operating unit. Alternative embodiments are conceivable in which the sensor electronics and the operating unit are designed for wireless communication. In such an instance, a portable operating device such as a portable computer, tablet computer, smart phone, data glasses, or a smartwatch can serve as the operating unit.

In the simplest case, the sensor electronics 7, 8, 9, 10 serve to transmit electrical signals generated by the transducers as measurement signals to the operating unit 2 in a format that can be processed by the operating unit 2. In addition, the sensor electronics 7, 8, 9, 10 can be designed to amplify and digitize the signal from the transducer. They can comprise a microprocessor that enables additional functions such as further processing the measurement signal provided by the transducer, and/or performing or supporting diagnostic functions of the sensor unit. In addition, the sensor electronics 7, 8, 9, 10 can have a memory in which information is saved that relates to the associated sensor unit 3, 4, 5, 6, such as a sensor ID, calibration data, operating hours meter, timer, information on a recommended service interval for the sensor unit, etc. In this case, the operating unit 2 can be designed to read out data from the memory and archive data in the memory that is determined or updated over the course of operation.

The operating unit 2 in the present example is a measuring transducer with four inputs by means of which the sensor units 3, 4, 5, 6 are connected. They comprise at least one processor and memory, in which are saved data and software that can be run by the processor which serve to determine measured values from the signals of the sensor units 3, 4, 5, 6 and to display the measured values. The operating unit 2 has a display 11 for displaying the measured values, as well as additional parameters or information. The operating unit 2 further comprises several keys 12 by which a user can select different views or menus and display them on the display, and can enter commands and information and set parameters. The operating unit 2 can have a communication interface for wireless or wired communication with other devices such as a higher-level unit or a cloud. In this manner, it is possible for the operating unit 2 to transmit measured values to a higher-level unit such as a process control center, or to have access to information, data, or software from the cloud that may not be available in the memory of the operating unit 2.

The operating unit 2 in the present example is designed to run some of the routines serving to diagnose and service the connected sensor units 3, 4, 5, 6. Among other things, the software that can be run by the operating unit comprises a service timer. This is a program routine that determines and displays the remaining time until a subsequent service measure. A service interval that is individually specified for each sensor unit is included in the calculation of the remaining time until the next service measure, along with the time that has passed since a last-performed service measure for the sensor unit determined by the operating unit time 2, e.g., by means of an internal clock generator. The service measure can, for example, be a calibration. The service interval can be specified for each sensor unit 3, 4, 5, 6 by an input from a user. Alternatively or in addition, the operating unit 2 can access a database in which a recommended service interval is archived for types of service sensor units that can be used with the operating unit 2. In this case, the operating unit 2 can propose to the user the service intervals recommended for the sensor type of the connected sensor units 3, 4, 5, 6, which the user can then specify for the service timer by confirming. In an alternative embodiment, it is also possible for the operating unit 2 to read out the identifiers of the sensor units 3, 4, 5, 6 from the memories of the sensor electronics 7 8, 9, 10 of the sensor units 3, 4, 5, 6, by means of which, possibly while accessing the aforementioned database, the sensor type of the respective sensor units and the service interval recommended for them are determined, and automatically used for the service timer.

The software that can be run by the operating unit 2 furthermore comprises an algorithm for calculating a state of the connected sensor units 3, 4, 5, 6, in which, depending upon the sensor type of the respective sensor unit, several current sensor-specific parameter values and/or a history of values of sensor-specific parameters are included. Possible current values that are included in the calculation of the state of the sensor unit 3 comprising a pH glass electrode are, for example, the impedance of the pH-sensitive glass membrane or the response time. A leakage current is possible as the current quantity in the state of the second sensor unit 4 that comprises an ISFET. With the sensor units 5, 6 as well, leakage current or other control parameters can also be included in the state calculation for the conductivity measurement.

For example, calibration parameters that are regularly determined when calibrating the sensor units, such as the zero point and the slope of the sensor characteristic, are possible parameters whose history is included when determining the sensor unit state. The values determined over the service life of a sensor unit 3, 4, 5, 6 during repeated calibrations can be archived in a memory of the sensor electronics 7, 8, 9, 10 and read out therefrom to determine the state of the sensor unit 3, 4, 5, 6. Additional history data that can be included in the state of the sensor unit 3, 4, 5, 6 can be the number of operating hours during which the sensor unit 3, 4, 5, 6 was exposed to high temperatures or high pH values or low temperatures. To detect this history data, the software of the operating unit 2 can comprise an operating hours meter that, by using temperature data of the medium and the pH values measured by the first sensor unit 3 and/or the second sensor unit 4, determines in a threshold value comparison the periods of time in which specified temperature threshold values have been exceeded and pH threshold values have been exceeded or undershot, and these periods of time are added up. The temperature data of the medium can be determined by the operating unit 2 via temperature sensors integrated in the sensor unit 3, 4, 5, 6 (not marked in FIG. 1).

Either by using information on the sensor type of the connected sensor units 3, 4, 5, 6 entered by the user, or by using the connected sensor units 3, 4, 5, 6 in the memory of the sensor electronics 7, 8, 9, 10, the operating device 2 selects a calculation rule that is individually adapted for each sensor type and is depicted in an algorithm of the software to determine the state of each sensor unit 3, 4, 5, 6. The calculation rule indicates the values that are included in the calculation and how they are linked to each other, in order to always determine a single value representing the state of the sensor unit 3, 4, 5, 6.

Figure 2:
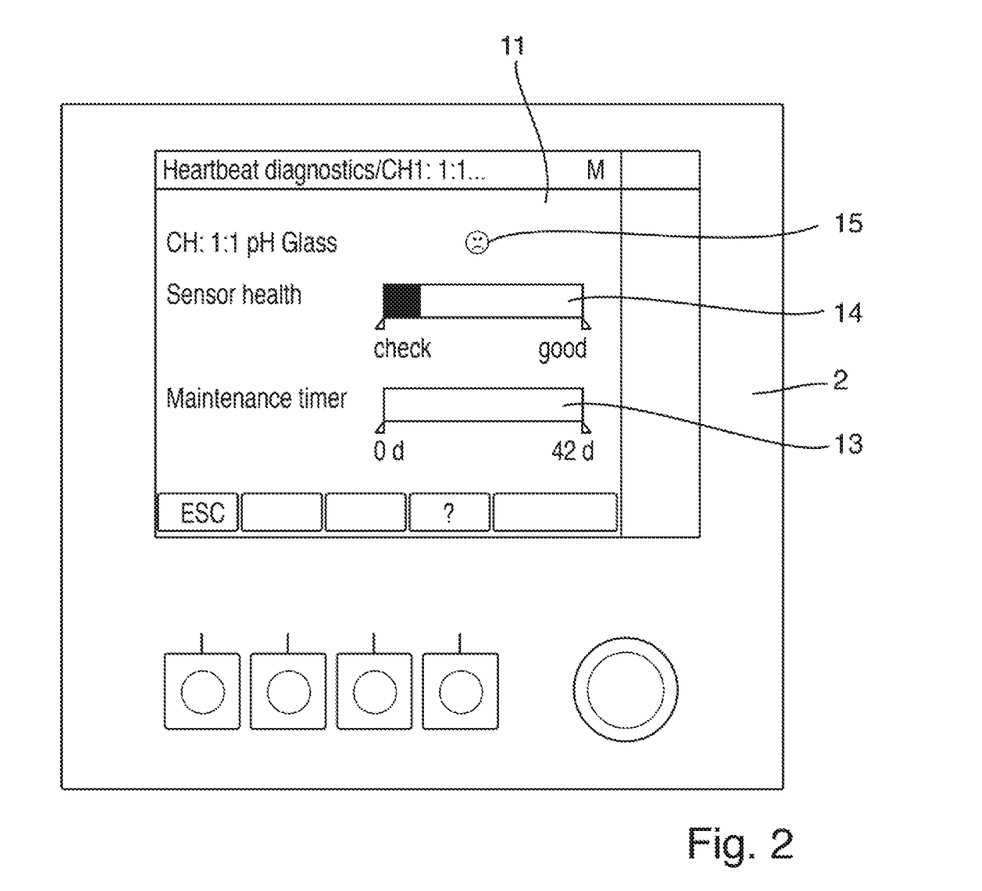
FIG. 2 shows a representation of a display relating to one of the pH sensor units on a display of the operating device of the measurement site presented in FIG. 1.

The values of the service timer determined in this manner and the state of the sensor units 3, 4, 5, 6 are regularly updated and presented on the display 11. This is illustrated in FIG. 2 for the first sensor unit 3, which comprises a pH glass electrode. There, the display 11 can be seen, in which a view of the diagnostic data ("Heartbeat diagnostics") of the first sensor unit 3 is selected. Corresponding views of the other sensor units 4, 5, 6 can be selected on the display 11 using the keys 12. The current value of the service timer (maintenance timer) is presented in a bar 13. In the display which can be seen in FIG. 2, maintenance has just been performed; consequently, a full 42 days are available until the next maintenance. The current value of the state of the sensor unit 3 (sensor health) is presented in the overlying bar 14. This illustrates that the state of the sensor unit 3 corresponds to less than 25%.

To make it easier for the user to schedule future service measures, the software of the operating unit 2 comprises an additional algorithm that serves to determine the recommended action. To determine the recommended action, the algorithm selects one of several specified recommended actions, based upon the current values of the service timer and the state of the sensor unit 3. In the current example, three possible actions are specified, i.e., "no action necessary," "action soon necessary," and "action presently recommended." In a very simple example, the selection can be made as follows: The current value of the service timer is compared with a first threshold value, e.g., 1 day, and with a second threshold value, e.g., 5 days, that lies above the first threshold value. In addition, the current value of the sensor unit state is also compared with a first and a second value that lie above the first threshold value. If the threshold value comparisons reveal that at least one of the values lies below the first, bottom threshold value, the recommended action, "action presently recommended," is selected. If both or only one of the values lie between the first and second threshold values, the recommended action, "action soon necessary," is selected. If both values lie above the second threshold value, the recommended action, "no action necessary," is selected.

Of course, other solutions are conceivable; for example, additional weightings of the incoming values can be performed.

The determined recommended action is displayed on the display 11. In the present example, the recommended action is presented by means of a graphical symbol 15 (smiley). Since, in the current example, the state of the first sensor unit 3, at 25%, lies below the first threshold value, the graphical symbol 15 ("sad smiley") is displayed that stands for the recommended action value, "action presently recommended." The threshold values can be set as default values specified by the manufacturer of the sensor units. It is, however, also possible, based upon the legal specifications for the process in which the sensor units 3, 4, 5, 6 are used, or based upon empirical values with regard to this process, for a user to specify the threshold values himself by an entry in the operating unit 2. The threshold values—especially, the threshold values specified by the manufacturer—can be saved in the aforementioned memory of the sensor electronics 6, 7, 8, 9, so that they are always associated with the sensor unit 3, 4, 5, 6.

Based upon the described threshold value comparison, a time point at which the service action should be performed at the latest in order to ensure safe operation of the sensor unit can also be determined, in the event that the determined recommended action is "action soon necessary" or "action presently needed." The remaining time span up to that point can be additionally displayed on the display 11. It is also possible to display the remaining time span by, for example, a design of the symbol 15, e.g., a color or a flashing frequency of the symbol 15.

With the symbol 15 representing the recommended action, a user can therefore directly discern whether maintenance of the associated sensor unit is pending, and can plan accordingly. For this, in contrast to interpreting the diagnostic information accessible via the bars 13 and 14, no particular user experience, or knowledge of the process in which the measurement site 1 is used, or knowledge of the sensory units 3, 4, 5, 6 is needed.

Figure 3:
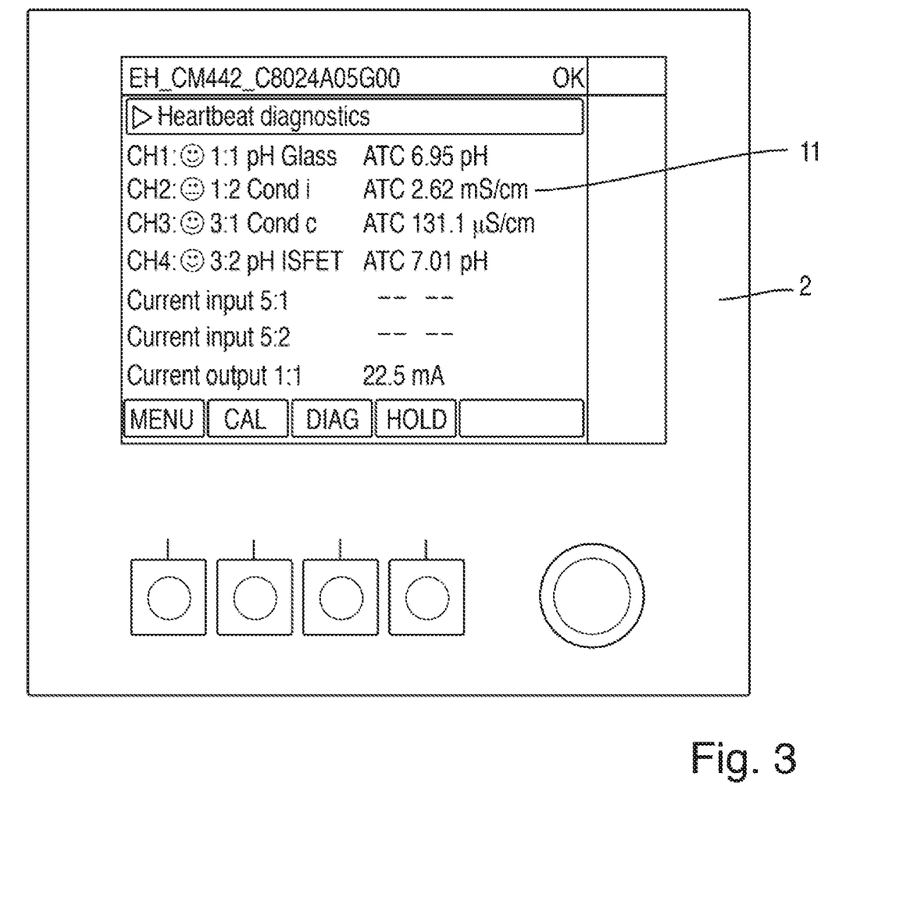
FIG. 3 shows a representation of a display relating to all sensor units on the display of the operating device of the measurement site presented in FIG. 1.

FIG. 3 portrays another view selected on the display 11 of the operating unit 2, in which the determined recommended actions are simultaneously presented in a list for all connected sensor units 3, 4, 5, 6. The first four lines 16, 17, 18, 19 of the displayed list present an identifier of the measuring channels (CH1, CH2, CH3, CH4), the current recommended action in the form of a graphic symbol, and the current measured values of the sensor units 3, 4, 5, 6. At a glance, the user can thereby ascertain whether there is a required action for one or more sensor units, and possibly undertake pending service measures or plan early on.

What is claimed is:

1. A method for operating a measurement site, comprising:
providing a measurement site including a sensor unit embodied to contact a medium and to take measurements resulting in measured values, the measurement site further including an operating unit having a display element, wherein the sensor unit is connected wirelessly or by wire to the operating unit for communication;

determining a first value representing a remaining time span up to a specified time point for a maintenance measure to be performed on the sensor unit;
determining a second value representing a current state of the sensor unit;
determining a third value based at least upon the first value and the second value and representing a recommended action with regard to the sensor unit; and
displaying the third value, a symbol derived from the third value, or a signal derived from the third value using the display element;
wherein determining the first value includes comparing a time span that has passed since a last-performed maintenance of the sensor unit with a specified value of a service interval specified for the sensor unit,
wherein maintenance is in a subset of types of service.

2. The method according to claim 1, wherein the second value is determined from current values of parameters correlated with the state of the sensor unit, and/or from values, repeatedly detected in the past, of parameters that represent a development of the state of the sensor unit, and/or a thermal and/or chemical load on the sensor unit occurring during a service life of the sensor unit.

3. The method according to claim 1, wherein determining the third value includes comparing the first value and the second value with one or more threshold values, and wherein, based upon the result of the comparisons with the one or more threshold values, selecting the third value from several different specified values representing different recommended actions.

4. The method according to claim 1, wherein the third value is displayed as a signal visually detectable by a user.

5. The method according to claim 1, wherein the display element includes a display, and the third value is displayed on the display as a symbol that is visually detectable by a user.

6. The method according to claim 1, wherein the measurement site further includes several sensor units connected to the operating unit for communication, and wherein, for each of the several sensor units, the method further comprises:
determining a first value representing a remaining time span up to a specified time point for a maintenance measure to be performed on the sensor unit;
determining a second value representing a current state of the sensor unit;
determining a third value based at least upon the first value and the second value and representing a recommended action with regard to the sensor unit; and
outputting the third value using the display element.

7. The method according to claim 6, wherein a first sensor unit of the several sensor units belongs to a first sensor type, and wherein a second sensor unit of the several sensor units belongs to a second sensor type different from the first sensor type,
wherein for the first sensor unit the first value is determined by comparing a time span that has passed since a last-performed maintenance of the first sensor unit with a specified value of a first service interval, and using a first calculating rule, the second value is determined from current values of first parameters correlated with the state of the first sensor unit, and/or from values, repeatedly detected in the past, of the first parameters that represent a development of the state of the first sensor unit, or a load on the first sensor unit occurring during an operational period of the first sensor unit, and wherein for the second sensor unit the first value is determined by comparing a time span that has passed since a last-performed maintenance of the second sensor unit with a specified value of a second service interval that differs from the first service interval, and using a second calculation rule that differs from the first calculation rule, the second value is determined from current values of second parameters correlated with the state of the second sensor unit, and/or from values, repeatedly detected in the past, of the second parameters that represent a development of the state of the second sensor unit, or a load on the second sensor unit occurring during an operational period of the second sensor unit.

8. The method according to claim 6, wherein the display element includes a display, the method further comprising:
presenting together on the display in a combined list the third values determined for each of the several sensor units and an identifier of each of the several sensor units.

9. The method according to claim 1, wherein the maintenance measure is a calibration.

10. A method for operating a measurement site, comprising:
providing the measurement site including a sensor unit embodied to contact a medium and to take measurements resulting in measured values, the measurement site further including an operating unit having a display element, wherein the sensor unit is connected wirelessly or by wire to the operating unit for communication;
determining a first value representing a remaining time span up to a specified time point for a maintenance measure to be performed on the sensor unit;
determining a second value representing a current state of the sensor unit;
determining a third value based at least upon the first value and the second value and representing a recommended action with regard to the sensor unit; and
displaying the third value, a symbol derived from the third value, or a signal derived from the third value using the display element;
wherein determining the third value includes comparing the first value and the second value with one or more threshold values, and wherein, based upon the result of the comparisons with the one or more threshold values, selecting the third value from several different specified values representing different recommended actions
wherein maintenance is in a subset of types of service;
wherein when the third value represents a recommended action that includes the performance of a service measure on the sensor unit, the method further comprises:
determining a time point that lies in the future for performing the service measure.

11. The method according to claim 10, further comprising:
displaying on the display element the time point lying in the future, or a remaining time span up to the time point lying in the future, and/or
outputting a signal representing the remaining time span.

12. A measurement site, comprising:
a first sensor unit embodied to contact a medium for detecting measured values, the first sensor unit including a transducer configured to output an electrical signal dependent upon a value of a measurand and a sensor circuit configured to output the electrical signal of the transducer or a signal derived from the electrical signal of the transducer as a measurement signal; and an operating unit including electronics configured to receive and process the measurement signal, the electronics including a processor, a memory, and software stored in the memory, the operating unit further including a display element that can be controlled by the electronics, wherein the software is configured to
    determine a first value representing a remaining time span up to a specified time point for a maintenance measure to be performed on the sensor unit,
    determine a second value representing a current state of the sensor unit,
    determine a third value based at least upon the first value and the second value and representing a recommended action with regard to the sensor unit, and
    display the third value, a symbol derived from the third value, or a signal derived from the third value using the display element;
    wherein determining the first value includes comparing a time span that has passed since a last-performed maintenance of the sensor unit with a specified value of a service interval specified for the sensor unit;

wherein maintenance is in a subset of types of service.

13. The measurement site according to claim 12, wherein the operating unit is connected by wire or wirelessly to the first sensor unit.

14. The measurement site according to claim 12, further comprising:
    a second sensor unit,
    wherein the first sensor unit belongs to a first sensor type, and the second sensor unit belongs to a second sensor type different from the first sensor type,
    wherein for the first sensor unit the software is configured to
        determine the first value by a comparison of a time span that has passed since a last-performed maintenance of the first sensor unit with a specified value of a first service interval, and
        determine using a first calculation rule the second value from current values of first parameters correlated with the state of the first sensor unit, and/or from values, repeatedly detected in the past, of the first parameters that represent a development of the state of the first sensor unit, or a load on the first sensor unit occurring during a service life of the first sensor unit, and
    wherein for the second sensor unit the software is configured to
        determine the first value by a comparison of a time span that has passed since a last-performed calibration of the second sensor unit with a specified value of a second calibration interval that differs from the first calibration interval, and
        using a second calculation rule that differs from the first calculation rule, determine the second value from current values of second parameters correlated with the state of the second sensor unit, and/or from values, repeatedly detected in the past, of the second parameters that represent a development of the state of the second sensor unit, or a load on the second sensor unit occurring during a life of the second sensor unit.

* * * * *